US010168288B2

(12) United States Patent
Bueno et al.

(10) Patent No.: US 10,168,288 B2
(45) Date of Patent: Jan. 1, 2019

(54) SYSTEM FOR RADIOGRAPHY IMAGING AND METHOD OF OPERATING SUCH SYSTEM

(71) Applicant: General Electric Company, Schenectady, NY (US)

(72) Inventors: Clifford Bueno, Clifton Park, NY (US); Tamas Gschwendtner, Aberdeen (GB); George Gibson Chalmers, Peterhead (GB); Donald Seton Farquhar, Niskayuna, NY (US); Antonio Luigi Ibba, Florence (IT)

(73) Assignee: General Electric Company, Schenectady, NY (US)

( * ) Notice: Subject to any disclaimer, the term of this patent is extended or adjusted under 35 U.S.C. 154(b) by 109 days.

(21) Appl. No.: 14/860,197

(22) Filed: Sep. 21, 2015

(65) Prior Publication Data
US 2017/0082556 A1 Mar. 23, 2017

(51) Int. Cl.
*G01N 23/04* (2018.01)
*G01N 23/06* (2018.01)
(Continued)

(52) U.S. Cl.
CPC .............. *G01N 23/04* (2013.01); *G01N 23/06* (2013.01); *G01N 23/083* (2013.01);
(Continued)

(58) Field of Classification Search
CPC ........ G01N 23/04; G01N 23/06; G01N 23/08; G01N 23/083; G01N 23/087; G01N 2223/628; G01N 23/046; G01V 5/0016
(Continued)

(56) References Cited

U.S. PATENT DOCUMENTS 4,179,100 A * 12/1979 Sashin ..................... A61B 6/02
250/366
5,150,394 A * 9/1992 Karellas ............... A61B 6/4241
250/252.1
(Continued)

OTHER PUBLICATIONS

Alchian, Armen A. et al. Mathematics Dictionary: Multilingual Edition. Edited by Glenn James and Robert C. James. Princeton, New Jersey: D. Van Nostrand Company, Inc., 1960. p. 216.*
(Continued)

*Primary Examiner* — Allen C. Ho
(74) *Attorney, Agent, or Firm* — Peter A. Flynn; Ernest G. Cusick; Frank A. Landgraff (57) ABSTRACT

A radiography imaging system for generating images of a pipe assembly includes a radiation source for emitting rays. The pipe assembly includes at least one of a pipe, tubing, and a weld. The radiation source includes a radioactive isotope having an activity level within a range between about 1 Curie and about 40 Curies. The radiation source is positioned adjacent a portion of the pipe assembly. A detector is positioned opposite the radiation source. The portion of the pipe assembly is positioned between the radiation source and the detector such that the rays interact with the portion of the pipe assembly and strike the detector. The detector includes an imaging plate that is activated by illumination with the rays with an exposure within a range between about 0.5 Curie-minute and about 5 Curie-minutes of radiation. The imaging plate has a thickness within a range between about 5 mm and about 15 mm. The detector further includes an imaging unit for generating images based on information from the imaging plate. The imaging unit has a pixel pitch that is within a range between about 25 microns and about 100 microns.

20 Claims, 5 Drawing Sheets

(51) Int. Cl.
  *G01N 23/083* (2018.01)
  *G01N 23/087* (2018.01)
  *G01T 1/20* (2006.01)
(52) U.S. Cl.
  CPC ......... *G01N 23/087* (2013.01); *G01T 1/2018* (2013.01); *G01N 2223/628* (2013.01)
(58) Field of Classification Search
  USPC .................................. 378/51, 53, 54, 57–59
  See application file for complete search history.

(56) References Cited

U.S. PATENT DOCUMENTS

| | | | | |
|---|---|---|---|---|
| 5,465,284 A | * | 11/1995 | Karellas | A61B 6/4241 250/252.1 |
| 5,651,047 A | * | 7/1997 | Moorman | A61B 6/06 378/19 |
| 5,864,146 A | * | 1/1999 | Karellas | A61B 6/06 250/581 |
| 6,137,860 A | | 10/2000 | Ellegood et al. | |
| 6,213,849 B1 | | 4/2001 | Johnson et al. | |
| 6,320,931 B1 | * | 11/2001 | Arnold | A61B 6/4035 378/54 |
| 6,377,654 B1 | * | 4/2002 | Willems | G01B 15/025 250/358.1 |
| 6,420,724 B1 | * | 7/2002 | Struye | G21K 4/00 250/362 |
| 6,445,767 B1 | * | 9/2002 | Karellas | A61B 6/06 250/370.09 |
| 6,466,643 B1 | | 10/2002 | Bueno et al. | |
| 6,476,406 B1 | * | 11/2002 | Struye | G03B 42/02 250/583 |
| 6,490,339 B2 | * | 12/2002 | Mitchell | A61B 6/4216 378/62 |
| 6,504,169 B1 | * | 1/2003 | Leblans | A61B 6/4216 250/582 |
| 6,516,098 B2 | * | 2/2003 | Nonaka | H01L 27/00 257/E27.001 |
| 6,528,812 B1 | * | 3/2003 | Leblans | A61B 6/4216 250/581 |
| 6,600,806 B1 | * | 7/2003 | Istar | G01B 15/02 378/58 |
| 6,670,614 B1 | * | 12/2003 | Plut | A61B 6/037 250/363.01 |
| 6,859,513 B2 | * | 2/2005 | Sako | A61B 6/00 378/16 |
| 6,925,145 B2 | * | 8/2005 | Batzinger | G01N 23/18 378/4 |
| 7,092,486 B2 | * | 8/2006 | Olesen | G01B 15/025 378/54 |
| 7,122,807 B2 | * | 10/2006 | Andou | G03B 42/02 250/484.4 |
| 7,186,997 B2 | * | 3/2007 | Gebele | G03B 42/08 250/588 |
| 7,224,769 B2 | | 5/2007 | Turner | |
| 7,260,171 B1 | * | 8/2007 | Arenson | A61B 6/032 378/16 |
| 7,291,841 B2 | * | 11/2007 | Nelson | G01T 1/243 250/370.01 |
| 7,319,738 B2 | * | 1/2008 | Lasiuk | G01N 23/04 378/198 |
| 7,330,531 B1 | * | 2/2008 | Karellas | A61B 6/4241 250/370.09 |
| 7,405,406 B1 | | 7/2008 | Nagarkar et al. | |
| 7,440,543 B2 | * | 10/2008 | Morton | G01F 1/66 378/10 |
| 7,480,363 B2 | * | 1/2009 | Lasiuk | G01B 15/025 378/54 |
| 7,550,728 B2 | * | 6/2009 | Spahn | G01T 1/1611 250/363.02 |
| 7,573,034 B2 | * | 8/2009 | Heath | G03B 42/02 250/361 R |
| 7,592,600 B2 | * | 9/2009 | Maschke | G01T 1/1615 250/370.09 |
| 7,656,997 B1 | * | 2/2010 | Anjelly | G01N 23/04 378/59 |
| 7,692,156 B1 | * | 4/2010 | Nagarkar | G01T 1/1644 250/361 R |
| 7,734,325 B2 | * | 6/2010 | Vizard | A61B 5/0059 250/336.1 |
| 7,825,393 B2 | * | 11/2010 | Corby, Jr. | G01V 5/0016 250/582 |
| 7,869,569 B2 | * | 1/2011 | Karellas | A61B 6/4258 378/54 |
| 7,885,381 B2 | * | 2/2011 | Nagumo | G01B 15/025 378/41 |
| 7,912,273 B2 | * | 3/2011 | Survant | G01N 23/04 382/141 |
| 8,054,939 B2 | * | 11/2011 | Gordon, III | G01N 23/083 378/58 |
| 8,439,565 B2 | * | 5/2013 | Mastronardi | G01N 23/04 378/205 |
| 8,520,797 B2 | * | 8/2013 | Yamada | A61B 6/037 378/4 |
| 8,575,562 B2 | * | 11/2013 | Wuestenbecker | G01N 23/083 250/393 |
| 8,693,613 B2 | * | 4/2014 | Bueno | G01N 23/04 376/450 |
| 8,759,780 B2 | * | 6/2014 | Dobbs | G01B 15/02 250/360.1 |
| 8,767,912 B1 | * | 7/2014 | Alzaidi | G01B 15/02 250/268 |
| 8,774,349 B2 | * | 7/2014 | Muenker | G01N 23/046 378/21 |
| 8,816,291 B2 | * | 8/2014 | Hawver | G01N 23/203 250/370.09 |
| 8,923,478 B2 | * | 12/2014 | Knight | G01N 23/18 250/257 |
| 8,938,046 B2 | * | 1/2015 | Hunter | G01N 23/04 378/181 |
| 8,976,936 B1 | * | 3/2015 | Alzaidi | G01N 23/203 378/149 |
| 9,057,680 B2 | * | 6/2015 | Jung | G01N 23/046 |
| 9,086,306 B2 | * | 7/2015 | Polikhov | G01F 1/704 |
| 9,110,172 B2 | * | 8/2015 | Lalleman | G01V 5/0016 |
| 9,110,175 B2 | * | 8/2015 | Henry | G03B 42/02 |
| 9,161,732 B2 | * | 10/2015 | Takayama | A61B 6/032 |
| 9,217,720 B2 | * | 12/2015 | Prentice | B23K 31/125 |
| 9,341,582 B2 | * | 5/2016 | Nagumo | G01N 23/046 |
| 9,347,894 B2 | * | 5/2016 | Sims | A61B 5/0035 |
| 9,488,603 B2 | * | 11/2016 | Stock | G01N 23/04 |
| 9,524,546 B2 | * | 12/2016 | Nagashima | G01N 23/04 |
| 9,588,234 B2 | * | 3/2017 | Watson | G01T 1/2014 |
| 9,753,150 B2 | * | 9/2017 | Nygard | G01T 1/2018 |
| 9,869,647 B2 | * | 1/2018 | Featonby | G01N 23/18 |
| 9,897,558 B2 | * | 2/2018 | Bowdon | G01N 23/046 |
| 2007/0096031 A1 | | 5/2007 | Meier et al. | |
| 2012/0087467 A1 | * | 4/2012 | Tjugum | G01N 23/223 378/54 |
| 2012/0201347 A1 | | 8/2012 | Prentice et al. | |
| 2012/0201348 A1 | | 8/2012 | Knight et al. | |
| 2015/0373822 A1 | * | 12/2015 | Churchman | G01N 23/04 378/59 |

OTHER PUBLICATIONS

"Industrial Radiography Image forming techniques", GE Inspection Technologies, pp. 1-221, Jun. 1, 2008.
Oliveira et al., "Advantages of Computed Radiography Technique in casting inspection with high energies", 20th International Congress of Mechanical Engineering, Nov. 15-20, 2009.
Machado et al., "Analyze image quality and comparative study between conventional and computed radiography applied to the inspection of alloys", International Nuclear Atlantic Conference, Belo Horizonte, MG, Brazil, Oct. 24-28, 2011.
International Search Report and Written Opinion issued in connection with corresponding PCT Application No. PCT/US2016/05250 dated Nov. 21, 2016.

(56) References Cited

OTHER PUBLICATIONS

Spartiotis et al., "X- and Gamma Ray Imaging Systems based on CdTe-CMOS Detector Technology", Nuclear Science Symposium Conference Record, 2008. NSS '08. IEEE, pp. 518-522, Oct. 2008.
Zahirian, "Evaluating Non-Destructive Testing (NDT) Methods used for the Inspection of Flowlines on Offshore Production Facilities", University of Stavanger, pp. 1-95, 2011.
Henon, "Orbital welding of Christmas Tree assemblies for the terra Nova project", Arc Machines, Inc, http://www.arcmachines.com/node/1934, 2015.
"DIC100TH (Unique Tube to Tube sheet weld inspection system)", Ajat CdTe-CMOS X ray Imaging, http://www.ajat.fi/product/dic100th-unique-tube-to-tube-sheet-weld-inspection-system/ , pp. 0-1, 2015.

* cited by examiner

SYSTEM FOR RADIOGRAPHY IMAGING AND METHOD OF OPERATING SUCH SYSTEM

BACKGROUND

The field of the disclosure relates generally to radiography imaging systems and, more particularly, to using a radiography imaging system to generate images of a pipe assembly.

Radiography imaging systems use rays to image portions of a target. A radiation source of the radiography imaging systems emits the rays in a direction towards the target. Upon striking the target, some of the rays are absorbed by the target and some of the rays are scattered through interaction with the target. Some of the rays that are scattered by the target strike a sensor which is used to generate an image of the target. The resulting image shows internal portions of the target. Accordingly, radiography imaging is used to determine characteristics of the target that are incapable of determination by non-destructive visual inspection. However, radiography imaging systems emit radiation that poses a health risk to operators and other personnel that may unnecessarily encounter the radiation. Therefore, use of radiography imaging systems is carefully monitored and controlled to limit radiation exposure for personnel.

Pipe assemblies are routinely inspected using radiography imaging systems to determine characteristics of the pipe assemblies. One type of pipe assembly is a Christmas tree structure. Christmas tree structures are positioned on wellheads of oil and gas wells to control valving of the oil and gas wells. The Christmas tree structures include high-pressure metal pipes that have been welded together. Radiography testing is especially useful to inspect the numerous pipes, valves, and welds on the Christmas tree structures. For radiation safety, areas surrounding the pipe assemblies are evacuated while the pipe assemblies are inspected. However, evacuating the surrounding areas results in a loss of productivity.

Sometimes, the pipe assemblies are moved to a remote site for radiography imaging. However, moving the pipe assemblies also results in a loss of productivity. For example, in one instance, moving one pipe assembly to a remote site, inspecting the pipe assembly at the remote site, and returning the pipe assembly to the factory floor takes up to three days for each pipe assembly. Accordingly, moving and imaging four pipe assemblies at the remote site consumes twelve days. Alternately, radiography imaging of the four pipe assemblies without relocating the pipe assemblies consumes only two days for all four assemblies. Accordingly, moving the four pipe assemblies for radiography testing results in a ten day loss of productivity.

BRIEF DESCRIPTION

In one aspect, a radiography imaging system for generating images of a pipe assembly is provided. The pipe assembly includes at least one of a pipe, tubing, and a weld. The radiography imaging system includes a radiation source for emitting rays. The radiation source includes a radioactive isotope having an activity level within a range between about 1 Curie and about 40 Curies. The radiation source is positioned adjacent a portion of the pipe assembly. A detector is positioned opposite the radiation source. The portion of the pipe assembly is positioned between the radiation source and the detector such that the rays interact with the portion of the pipe assembly and strike the detector. The detector includes an imaging plate that is activated by illumination with the rays with an exposure within a range between about 0.5 curie-minute and about 5 Curie-minutes of radiation. The imaging plate has a thickness within a range between about 5 mm and about 15 mm. The detector further includes an imaging unit for generating images based on information from the imaging plate. The imaging unit has a pixel pitch that is within a range between about 25 microns and about 100 microns.

In another aspect, a pipe assembly manufacturing facility for assembling a plurality of pipe assemblies is provided. The pipe assembly manufacturing facility includes at least one assembly area for assembling the plurality of pipe assemblies and a radiography imaging system for generating images of the plurality of pipe assemblies. The radiography imaging system includes a radiation source for emitting rays. The radiation source is positioned adjacent to at least one pipe assembly of the plurality of pipe assemblies. The radiation source includes a radioactive isotope having an activity level within a range between about 1 Curie and about 40 Curies. A detector is positioned opposite the radiation source. A portion of the at least one pipe assembly of the plurality of pipe assemblies is positioned between the radiation source and the detector such that the rays interact with the portion of the at least one pipe assembly and strike the detector. The detector includes an imaging plate and an imaging unit. The imaging plate is activated by illumination with the rays with an exposure within a range between about 0.5 curie-minute and about 5 Curie-minutes of radiation. The imaging plate has a thickness within a range between about 5 mm and about 15 mm. The imaging unit generates images based on information from the imaging plate. The imaging unit has a pixel pitch that is within a range between about 25 microns and about 100 microns. The pipe assembly manufacturing facility further includes at least one inspection area for inspecting the at least one pipe assembly of the plurality of pipe assemblies using the radiography imaging system. The at least one inspection area is contiguous with the at least one assembly area. The at least one pipe assembly remains in the at least one inspection area during operation of the radiography imaging system.

In yet another aspect, a method of imaging a pipe assembly uses a radiography imaging system. The radiography imaging system includes a radiation source and a detector. The radiation source includes a radioactive isotope. The method includes mounting the radiography imaging system on the pipe assembly such that a portion of the pipe assembly is positioned between the radiation source and the detector. Rays are emitted from the radiation source such that the rays interact with the pipe assembly and strike the detector. The radioactive isotope has an activity level within a range between about 1 Curie and about 40 Curies. The pipe assembly is illuminated with the rays with an exposure within a range between about 0.5 Curie-minute and about 5 Curie-minutes of radiation. The imaging plate of the detector is activated with the rays and an image of the pipe assembly is generated.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The methods and systems described herein overcome at least some disadvantages of known radiography imaging systems by providing a radiography imaging system that emits a low level of radiation and has a high sensitivity imaging plate. As a result, a pipe assembly is inspected using the radiography imaging system without relocation to a remote site and without evacuating the areas surrounding the pipe assembly during the radiography imaging. In some embodiments, the radiography imaging system includes additional shielding to inhibit exposing personnel near the pipe assembly to radiation during radiography imaging. Moreover, the radiography imaging system described herein is sized and configured to position on portions of the pipe assembly having little clearance space.

Figure 1:
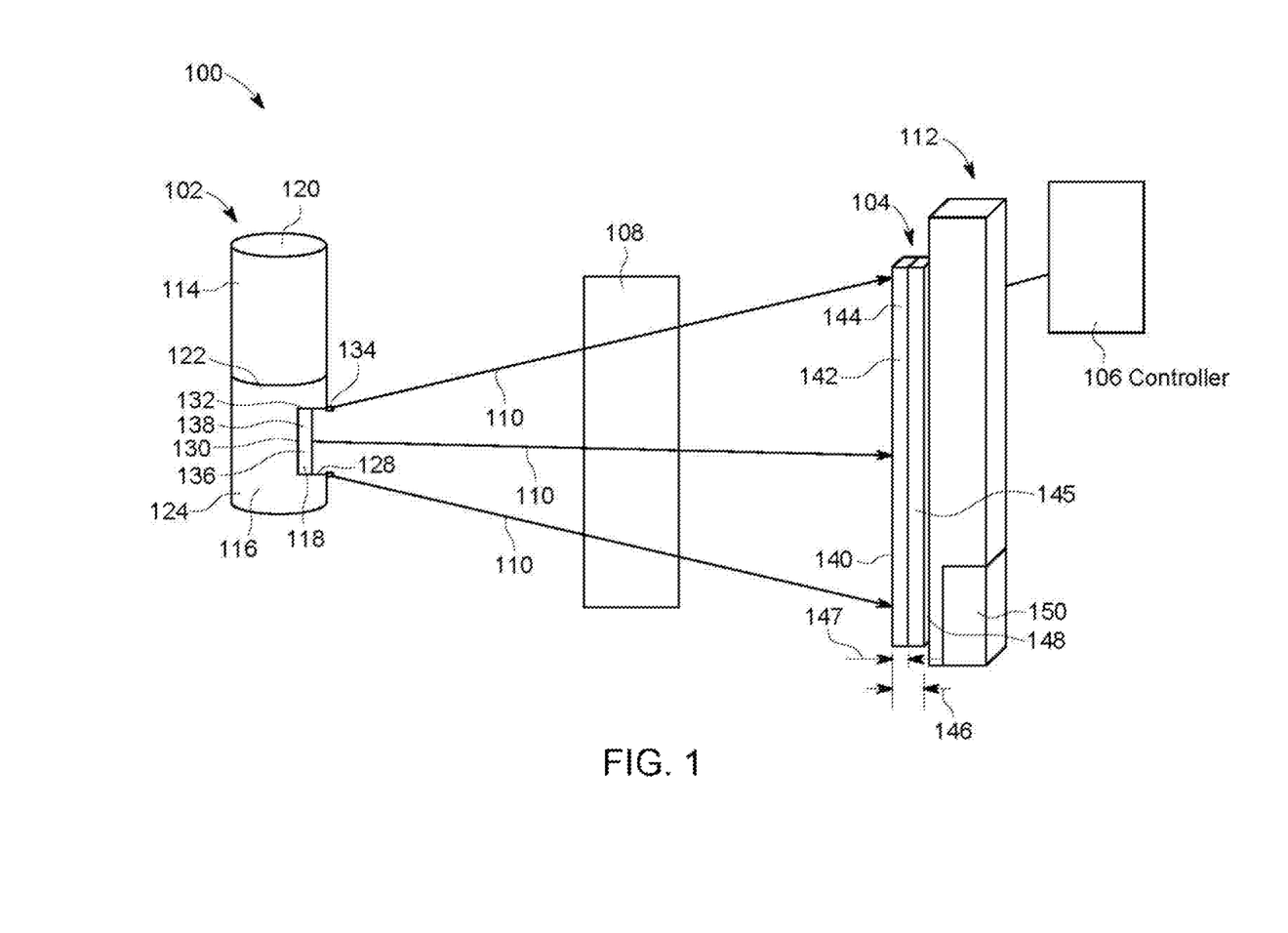
FIG. 1 is a perspective view of an exemplary radiography imaging system.

FIG. 1 is a perspective view of an exemplary radiography imaging system designated generally by the number 100. Radiography imaging system 100 includes a radiation source 102, a detector 104, and a controller 106. A target 108 is positioned between radiation source 102 and detector 104. In operation, radiation source 102 emits rays 110, e.g., pulses of photons, that travel towards target 108 and strike detector 104. Detector 104 includes an imaging unit 112 that produces images based on information generated from rays 110 striking detector 104. In the exemplary embodiment, rays 110 are gamma rays having an energy between about 100 kiloelectron-volts (keV) and about 500 keV. In alternative embodiments, radiation source 102 emits any rays 110 at any energy that enable radiography imaging system 100 to function as described herein.

In the exemplary embodiment, radiation source 102 includes a guide tube 114, a close proximity container 116, and a pellet 118. Guide tube 114 has an inlet end 120, an outlet end 122, and a sidewall 124 extending between inlet end 120 and outlet end 122. Sidewall 124 inhibits radiation escaping guide tube 114 as pellet 118 travels through guide tube 114 from inlet end 120 to outlet end 122. In the exemplary embodiment, sidewall 124 includes at least one layer of tungsten and is curved to form a cylindrical shape with a diameter that is substantially constant from inlet end 120 to outlet end 122. In alternative embodiments, the diameter of sidewall 124 varies from inlet end 120 to outlet end 122. In alternative further embodiments, sidewall 124 has any shape and includes any materials that enable radiation source 102 to function as described herein. Preferably, guide tube 114 has a length between about 50 millimeters (mm) (2 inches (in.)) and about 250 mm (10 in.). In the exemplary embodiment, guide tube 114 has a length of approximately 152 mm (6 in.). The length of guide tube 114 reduces the time that pellet 118 is in guide tube 114 and, thereby, reduces radiation that is emitted from radiation source 102. Additionally, the length of guide tube 114 facilitates radiography imaging system 100 fitting in positions on pipe assembly 200 having little clearance space. In alternative embodiments, guide tube 114 has any length that enables radiation source 102 to function as described herein. In further alternative embodiments, guide tube 114 is omitted.

In the exemplary embodiment, pellet 118 moves from guide tube 114 into interior space 128. An opening 130 extends through sidewall 124 such that radiation from pellet 118 in interior space 128 is channeled through sidewall 124 and directed towards target 108 and detector 104. A shutter 132 closes opening 130 to inhibit rays 110 from escaping interior space 128 through opening 130 when shutter 132 is in a closed position. Accordingly, an operator uses shutter 132 to selectively emit rays 110 from radiation source 102 by moving shutter 132 between an open position and the closed position. A collimator 134 surrounds opening 130 to focus rays 110 on target 108 and detector 104. As a result, close proximity container 116 reduces unnecessary and stray emissions of rays 110.

In the exemplary embodiment, pellet 118 includes a radioactive isotope 136 surrounded by a casing 138. Casing 138 reduces radiation emissions from radioactive isotope 136 to facilitate handling radioactive isotope 136. In the illustrated embodiment, casing 138 is tungsten and/or stainless steel. In alternative embodiments, casing 138 is any material that enables pellet 118 to function as described herein. In the exemplary embodiment, radioactive isotope 136 is selenium 75, which emits gamma rays. In some embodiments, radioactive isotope 136 has an activity level between about 1 Curie and about 40 Curies. In further embodiments, radioactive isotope 136 has an activity level between about 1 Curie and about 6 Curies. In the exemplary embodiment, radioactive isotope 136 has an activity level of about 1 Curie. Preferably, target 108 is exposed to radiation between about 0 Curie-minutes and about 10 Curie-minutes. More preferably, target 108 is exposed to radiation between about 0.5 curie-minutes and about 5 Curie-minutes. In the exemplary embodiment, target 108 is exposed to radiation for approximately 5 Curie-minutes. As a result, radiography imaging is performed with minimal or no shielding while people work in surrounding areas.

In alternative embodiments, radioactive isotope 136 is any material that enables operation of radiography imaging system 100 as described herein. In further alternative embodiments, radiation source 102 emits electromagnetic radiation such that radiography imaging system 100 acts as an x-ray imaging device. For example, in some embodiments, radiation source 102 emits electromagnetic radiation having energies between about 50 kilovolts (kV) and about 200 kV.

In the exemplary embodiment, detector 104 includes a face plane 140, an imaging plate 142, imaging unit 112, and a housing 144. Housing 144 at least partially encloses face plane 140, imaging plate 142, and imaging unit 112. In the exemplary embodiment, housing 144 has a rectangular shape and tightly encloses detector 104 to facilitate detector 104 fitting into spaces having little clearance space. In alternative embodiments, housing 144 has any shape that enables detector 104 to function as described herein. In further embodiments, at least some components of detector 104, such as electronics, are disposed outside housing 144 in a flex casing to facilitate mounting detector 104 in tight spaces.

In the exemplary embodiment, imaging plate 142 has a thickness 146 measured between face plane 140 and a surface 148 of imaging unit 112. Imaging plate 142 includes a phosphor screen for activation by rays 110 and the phosphor screen has a thickness 147. In alternative embodiments, imaging plate 142 is any material that enables detector 104 to function as described herein. In the exemplary embodiment, thickness 147 of the phosphor screen affects the resolution of an image produced from reading imaging plate 142. Specifically, decreasing the thickness of phosphor in imaging plate 142 increases the image resolution of an image produced from reading imaging plate 142. However, the percentage of rays 110 that are not absorbed by imaging plate 142 increases as thickness 147 decreases. The increased percentage of rays 110 that are not absorbed by imaging plate 142 increases the radiation in the areas surrounding radiography imaging system 100 and, thereby, poses a safety risk to people in the surrounding areas. In contrast, increasing thickness 147 increases the ability of imaging plate 142 to absorb a greater portion of rays 110. Therefore, the photon flux level required to produce an image is reduced as thickness 147 increases. In some embodiments, phosphor screen has thickness 147 between about 5 mm and about 15 mm. In the exemplary embodiment, the phosphor screen has thickness 147 of approximately 9 mm. In alternative embodiments, the phosphor screen has any thickness that enables detector 104 to function as described herein. As a result, due at least in part to thickness 147, radiography imaging system 100 uses a lower photon flux level and emits less rays 110 to surrounding areas.

In the illustrated embodiment, detector 104 further includes a fiber optic faceplate 145 that acts as a zero-depth window and transfers an image pixel by pixel, i.e., fiber by fiber, from imaging plate 142 to imaging unit 112. As a result, face plane 140 facilitates controlling photon flux levels on imaging plate 142. As used herein, the term "photon flux level" refers to the number of photons that are incident on an area. In alternative embodiments, face plane 140 is omitted. For example, in some embodiments, imaging plate 142 acts as the scintillator and directly transfers the image to imaging unit 112. In the exemplary embodiment, fiber optic faceplate 145 facilitates removing and replacing the phosphor screen and protects imaging unit 112.

In the exemplary embodiment, imaging unit 112 is coupled to imaging plate 142 such that imaging unit 112 generates an image after rays 110 activate imaging plate 142. In alternative embodiments, detector 104 utilizes direct conversion. In direct conversion, rays 110 are converted directly to a charge of electrons using a photoconductor without an intermediary light stage. In alternative embodiments that utilize direct conversion, imaging unit 112 utilizes the charged electrons from activated imaging plate 142 to produce a radiography image.

In the exemplary embodiment, imaging unit 112 produces an image with pixels and has a predetermined pixel pitch. Pixel pitch is a measurement of the pixel density used by imaging unit 112 to produce the image. Specifically, pixel pitch is a measure of the size of an individual pixel used by an imaging unit. Therefore, pixel pitch determines resolution of the image produced by imaging unit 112. In one embodiment, the pixel pitch of imaging unit 112 is between about 25 microns and about 100 microns. In the exemplary embodiment, the pixel pitch of imaging unit 112 is approximately 50 microns. In alternative embodiments, imaging unit 112 has any pixel pitch that enables operation of radiography imaging system 100 as described herein.

Typically, to produce an image having a resolution close to the resolution capacity of imaging unit 112, imaging plate 142 is matched with imaging unit 112. However, in the exemplary embodiment, imaging plate 142 does not have a resolution that matches the very fine pixel pitch of imaging unit 112. In an embodiment, the phosphor screen is a coarse phosphor screen that corresponds to imaging unit 112 having a pixel pitch between about 150 microns and about 225 microns. In one embodiment, imaging plate 142 corresponds to imaging unit 112 having a pixel pitch of about 200 microns. Therefore, imaging unit 112 reads imaging plate 142 and generates an image with a resolution lower than the capacity of imaging unit 112. As a result, radiography imaging system 100 uses a lower photon flux level to produce a radiography image due to the combination of imaging plate 142 having a coarse image resolution capacity and imaging unit 112 having a very fine pixel pitch.

For example, in some embodiments, detector 104 generates an image having a pixel pitch of between about 25 microns ($1 \times 10^{-3}$ in.) and about 125 microns ($5 \times 10^{-3}$ in.) due to the combination of imaging plate 142 and imaging unit 112. In the exemplary embodiment, imaging unit 112 generates an image having a pixel pitch of about 100 microns ($4 \times 10^{-3}$ in.). Preferably, detector 104 generates an image with an area between about 25 mm×25 mm (1 in.×1 in.) and about 102 mm×102 mm (4 in.×4 in.) In the exemplary embodiment, detector 104 generates an image with approximately a 51 mm×102 mm (2 in.×4 in.) area. In alternative embodiments, imaging unit 112 generates an image having any pixel pitch, area, and spatial resolution that enable radiography imaging system 100 to function as described herein.

Figure 2:
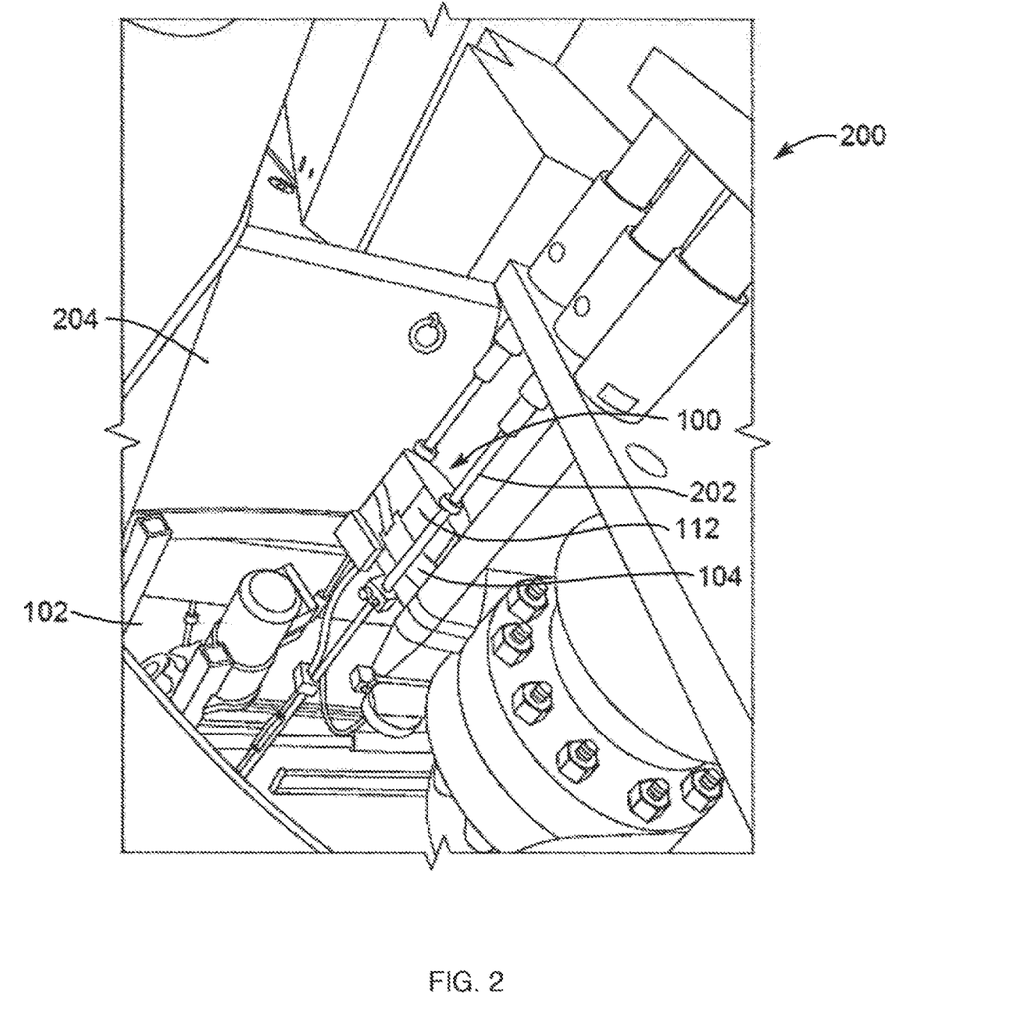
FIG. 2 is a partial perspective view of the radiography imaging system shown in FIG. 1 positioned on an exemplary pipe assembly.

FIG. 2 is a partial perspective view of radiography imaging system 100 positioned on an exemplary pipe assembly, designated generally by the number 200. In the exemplary embodiment, radiography imaging system 100 is positioned at least partially on pipe assembly 200 to generate images of a pipe 202 of pipe assembly 200. In alternative embodiments, radiography imaging system 100 is used to generate images of at least one of pipe 202, tubing, and a weld. In the exemplary embodiment, detector 104 is positioned adjacent pipe 202 and radiation source 102 is positioned opposite detector 104 such that rays 110 (shown in FIG. 1) emitted by radiation source 102 interact with pipe 202 and strike detector 104. Radiation source 102 and detector 104 are securely mounted on pipe assembly 200 and coupled to controller 106 (shown in FIG. 1) such that an operator operates radiography imaging system 100 from a distance safely removed from rays 110. Additionally, pipe assembly 200 includes temporary shielding 204 positioned to shield the operator from radiation. In alternative embodiments, due to the low level of radiation emitted by radiography imaging system 100, temporary shielding 204 is omitted.

Referring back to FIG. 1, in the exemplary embodiment, imaging unit 112 includes processor 150 to facilitate processing the radiography image. The radiography image is used to evaluate components of pipe assembly 200. For example, the operator inspects the radiography image to evaluate a weld on pipe assembly 200 by determining features such as pores in the weld, depth of weld penetration, and the resulting wall thickness. In at least some embodiments, radiography imaging system 100 images components of pipe assembly 200 having at least one of an outer diameter of up to 0.75 in. (19 mm), a wall thickness in the range of about 0.065 in. (1.65 mm) to about 0.086 in. (2.18 mm), and a maximum welded wall thickness of about 0.125 in. (3.175 mm). In one embodiment, processor 150 facilitates post processing the image to show all the relevant features in the image at one time. In the exemplary embodiment, processor 150 calculates and corrects for variables such as background levels in detector 104, pixel-to-pixel variations, and exposure times. Additionally, in some embodiments, processor 150 averages multiple images of the same portion of pipe assembly 200 together to correct for signal-to-noise levels and produce a more accurate cumulative image. In alternative embodiments, processor 150 is any processor that enables imaging unit to function as described herein. In further embodiments, processor 150 incorporates metadata into the images.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Figure 3:
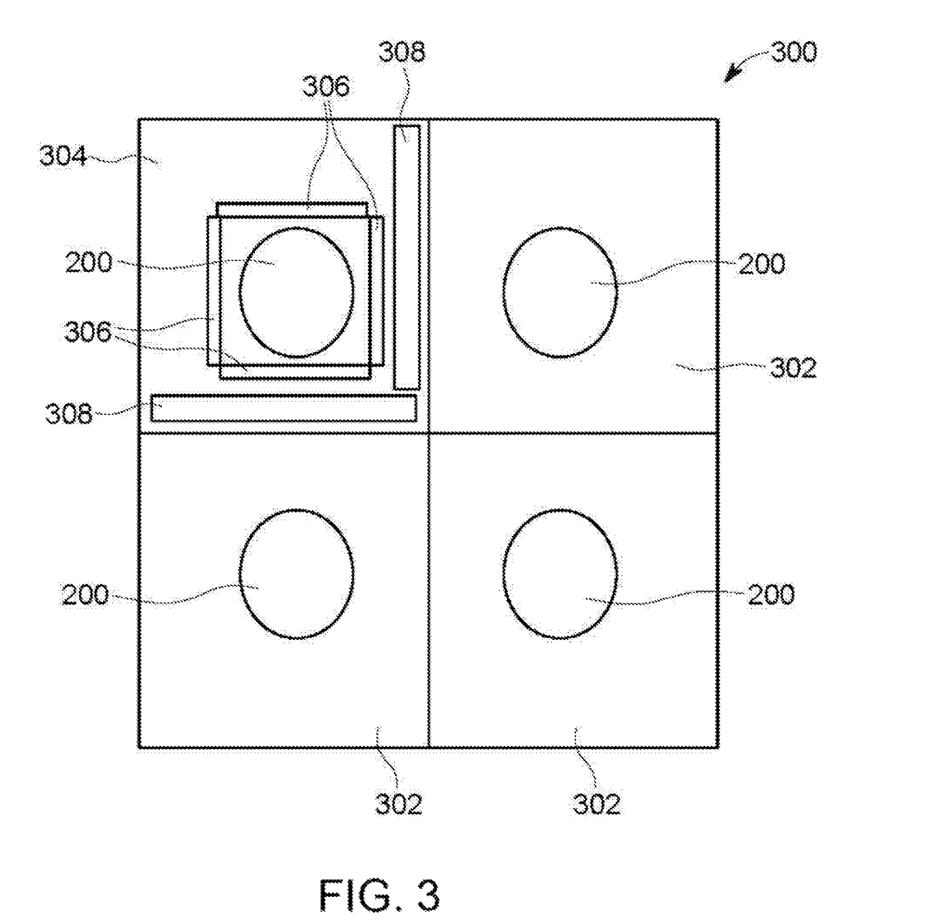
FIG. 3 is a plan view of an exemplary pipe assembly manufacturing facility for pipe assemblies.

FIG. 3 is a schematic view of a pipe assembly manufacturing facility 300 for assembling a plurality of pipe assemblies 200. Pipe assembly manufacturing facility 300 includes a plurality of assembly areas 302 for assembling pipe assemblies 200 and at least one inspection area 304 for inspecting pipe assemblies 200 using radiography imaging system 100. For example, pipe assemblies 200 are positioned in assembly areas 302 during assembly and pipe assembly 200 is positioned in inspection area 304 during inspection. Assembly areas 302 are converted to inspection areas 304 when pipe assemblies 200 are ready for inspection and inspection areas 304 are converted to assembly areas after inspection of pipe assembly 200. In the exemplary embodiment, assembly areas 302 are contiguous with inspection area 304. The lower energies and lower photon flux levels utilized in radiography imaging system 100 reduces the exclusion zone around pipe assembly 200 during testing. Therefore, pipe assembly 200 is not removed to a remote site for inspection. Additionally, pipe assembly manufacturing facility 300, including assembly areas 302 and inspection area 304, is not evacuated during testing. Therefore, work in assembly areas 302 continues while pipe assembly 200 is inspected using radiography imaging system 100. In some embodiments, at least some personnel are excluded from pipe assembly manufacturing facility 300 during testing. For example, in some embodiments, nonessential personnel are excluded from pipe assembly manufacturing facility 300 for about 1 hour to about 2 hours during imaging.

In the illustrated embodiment, inspection area 304 further includes shielding 306 and barricades 308. Shielding 306 is a dense material that inhibits rays 110 passing through shielding 306. Shielding 306 is positioned around pipe assembly 200 in any manner that inhibits rays 110 from passing to portions of inspection area 304 and surrounding assembly areas 302. In alternative embodiments, shielding 306 is omitted due to the low energies and photon flux levels used by radiography imaging system 100. In the exemplary embodiment, barricades 308 obstruct entry into inspection area 304 and warn personnel that pipe assembly 200 is undergoing radiography imaging. Accordingly, barricades 308 are any barriers that obstruct a pathway and provide warning. For example, in some embodiments, barricades 308 are, without limitation, signs, cones, barriers, ropes, lights, and tape.

In alternative embodiments, pipe assembly 200 is inspected on-site in the installation location of pipe assembly 200, such as an off shore location prior to submersion of pipe assembly 200. Radiography imaging system 100 facilitates inspecting pipe assembly 200 on-site because of the low energies of rays 110 and the compact size of radiography imaging system 100. During inspection on-site, work continues in areas surrounding inspection area 304 with little to no interruption.

Figures 4, 5A:
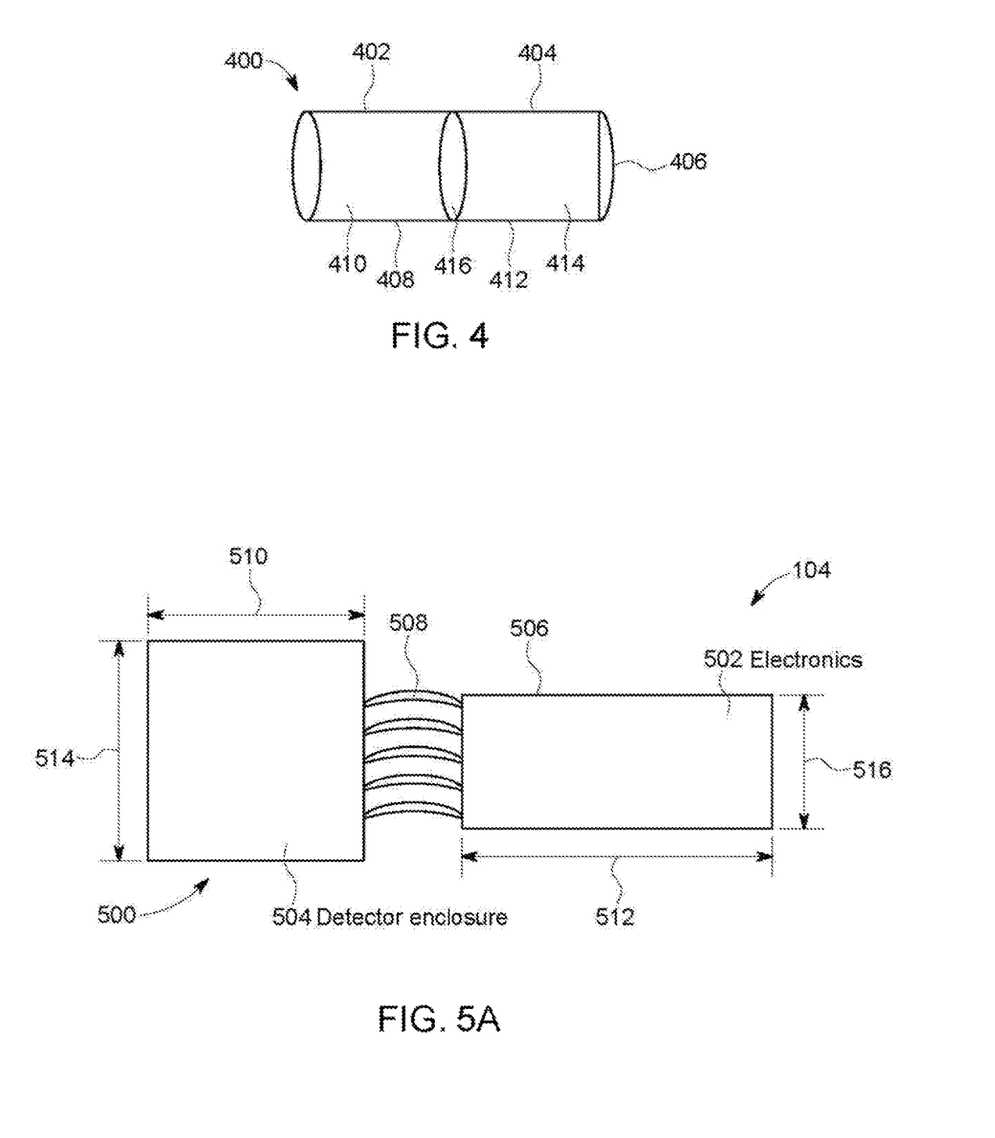
FIG. 4 is a section view of an exemplary radiation source for use in the radiography imaging system shown in FIG. 1.
FIG. 5A is a perspective view of an exemplary casing for an exemplary detector 104 used in the radiography imaging system shown in FIG. 1.

FIG. 4 is a section view of an alternate radiation source 400 for use in radiography imaging system 100. Radiation source 400 includes a container 402, a guide tube 404, and a collimator head 406. Container 402 includes a container sidewall 408 defining an interior space 410. Similarly, guide tube 404 includes a guide tube sidewall 412 defining an interior space 414. Container sidewall 408 and guide tube sidewall 412 include shielding to inhibit rays 110 passing through container sidewall 408 and guide tube sidewall 412. In the exemplary embodiment, both container 402 and guide tube 404 have substantially cylindrical shapes. In alternative embodiments, container 402 and guide tube 404 have any shape that enables radiation source 400 to function as described herein. In some embodiments, guide tube 404 has a diameter in the range between about 13 mm (0.5 in.) and about 127 mm (5 in.) and a length in the range between about 127 mm (5 in.) and about 381 mm (15 in.). In the exemplary embodiment, guide tube 404 has a diameter of approximately 1 in. (25 mm) and a length of approximately 10 in. (254 mm). In alternative embodiments, guide tube 404 is any size that enables radiation source 400 to function as described herein. The size and shape of guide tube 404 and radiation source 400 facilitates positioning radiation source 400 in locations having tight clearances.

In the exemplary embodiment, container 402 and guide tube 404 are coupled together such that pellet 118 moves between interior space 410 and interior space 414. A shutter 416 separates interior space 410 and interior space 414 and is selectively positionable between a closed position where movement of pellet 118 between interior space 410 and interior space 414 is obstructed and an open position where movement of pellet 118 between interior space 410 and interior space 414 is allowed. In the exemplary embodiment, collimator head 406 is a collimator having a substantially parabolic shape to focus rays 110 on target 108 and detector 104.

Figure 5B:
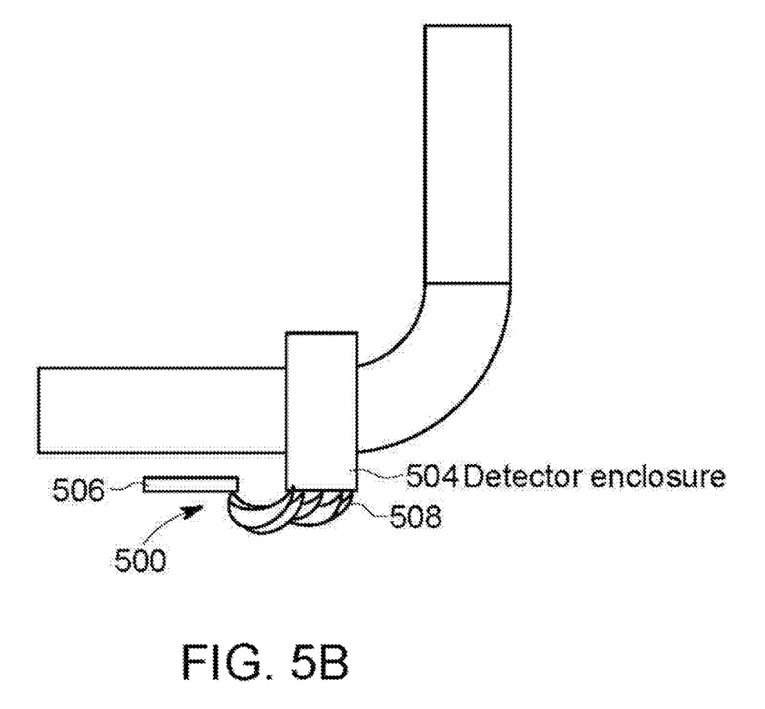
FIG. 5B is a perspective view of the casing shown in FIG. 5A in a flexed position.

FIG. 5A is a perspective view of a flex casing 500 for detector 104 for use in radiography imaging system 100. FIG. 5B is a perspective view of flex casing 500 in a flexed position. Detector 104 is enclosed in flex casing 500 to facilitate detector 104 mounting on locations where rigid components have a hard time fitting, such as on bends in pipes. In the exemplary embodiment, flex casing 500 separately encloses components of detector 104, such as electronics 502, to reduce the profile of detector 104. In alternate embodiments, any components of detector 104 have any enclosures that enable detector to function as described herein. In the exemplary embodiment, flex casing 500 comprises a detector enclosure 504, an electronics enclosure 506, and a coupling 508 extending between detector enclosure 504 and electronics enclosure 506. In the exemplary embodiment, coupling 508 is a plurality of flexible bands that enclose wires extending from detector enclosure 504 to electronics enclosure 506. In alternate embodiments, coupling 508 is any coupling mechanism that enables detector 104 to function as described herein. Each of detector enclosure 504 and electronics enclosure 506 have respective lengths 510,512, and widths 514,516. In some embodiments, lengths 510,512 are in the range between about 25 mm (1 in.) and about 610 mm (24 in.) and widths 514,516 are in the range between about 25 mm (1 in.) and about 610 mm (24 in.). In the exemplary embodiment, width 514 is approximately 30 mm (1.2 in.) and lengths 510 is approximately 30 mm (1.2 in.). In the exemplary embodiment, width 516 is approximately 25 mm (1 in.) and length 512 is approximately 60 mm (2.4 in.). In some embodiments, width 514 is equal to width 516 and/or length 510 is equal to length 512. In alternate embodiments, detector enclosure 504 and electronics enclosure 506 have any lengths and widths that enable detector 104 to function as described herein.

Referring to FIGS. 1-3, a method of inspecting pipe assembly 200 using radiography imaging system 100 includes positioning pipe assembly 200 in inspection area 304. In alternative embodiments shielding 306 is positioned around pipe assembly 200. In further alternative embodiments, barricades 308 are positioned around inspection area 304 to separate inspection area 304 from surrounding assembly areas 302. Radiography imaging system 100 is mounted on pipe assembly 200 such that a portion of pipe assembly 200 is positioned between radiation source 102 and detector 104. Pellet 118 is directed through guide tube 114 from inlet end 120 to outlet end 122 and into interior space 128 of close proximity container 116. Shutter 132 is moved to the open position such that rays 110 are emitted from radiation source 102 and travel towards target 108 and detector 104. Rays 110 interact with target 108 and strike detector 104. The portion of pipe assembly 200 that is imaged is exposed to between about 0.5 curie-minute and about 5 Curie-minutes of radiation. Detector 104 is activated by rays 110 and imaging unit 112 generates an image based on information from imaging plate 142. In some embodiments, the method is repeated to generate a composite radiography image of a section of pipe assembly 200. In the exemplary embodiment, the radiography image is inspected to determine characteristics of target 108. For example, in some embodiments, target 108 is a portion of pipe assembly 200 having a weld and the image is inspected to determine characteristics of the weld. In some embodiments, radiography imaging system 100 is repositioned and at least some of the above described steps are repeated to inspect different portions of pipe assembly 200.

The above-described radiography imaging system 100 overcomes at least some disadvantages of known radiography imaging systems by providing a radiography imaging system 100 that emits a low level of radiation and has a high sensitivity imaging plate 142. As a result, a pipe assembly 200 is inspected using the radiography imaging system 100 without relocation to a remote site and without evacuating the areas surrounding the pipe assembly 200 during the radiography imaging. In some embodiments, the radiography imaging system 100 includes additional shielding to inhibit exposing personnel near the pipe assembly 200 to radiation during radiography imaging. Moreover, the above described radiography imaging system 100 is sized and configured to position on portions of the pipe assembly 200 having little clearance space.

An exemplary technical effect of the methods, systems, and apparatus described herein includes at least one of: (a) decreasing the size of components such that the radiography imaging system 100 fits portions of the pipe assembly 200 having little clearance; (b) increasing durability of the radiography imaging system 100; (c) lowering the levels of radiation used for radiography imaging; (d) imaging a pipe assembly 200 without relocating the pipe assembly 200 to a remote site; (e) reducing the safety risk to personnel in areas surrounding the radiography inspection area 304; (f) decreasing the time required to generate and process an image of a pipe assembly 200; (g) increasing image quality of radiography imaging systems; and (h) processing an Image of the pipe assembly 200 to indicate relevant features of the pipe assembly 200.

Exemplary embodiments of apparatus and methods for operating a radiography imaging system 100 are described above in detail. The methods and apparatus are not limited to the specific embodiments described herein, but rather, components of systems and/or steps of the methods may be utilized independently and separately from other components and/or steps described herein. For example, the methods, systems, and apparatus may also be used in combination with other radiography systems, and the associated methods, and are not limited to practice with only the systems and methods as described herein. Rather, the exemplary embodiment can be implemented and utilized in connection with many other applications, equipment, and systems that may benefit from improved radiography.

Although specific features of various embodiments of the disclosure may be shown in some drawings and not in others, this is for convenience only. Moreover, references to "one embodiment" in the above description are not intended to be interpreted as excluding the existence of additional embodiments that also incorporate the recited features. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A radiography imaging system for generating images of a pipe assembly, the pipe assembly including at least one of a pipe, tubing, and a weld, said radiography imaging system comprising:
    a radiation source for emitting rays, said radiation source comprising a radioactive isotope having an activity level between 1 Curie and 40 Curies, said radiation source positioned adjacent a portion of the pipe assembly; and
    a detector positioned opposite said radiation source, the portion of the pipe assembly positioned between said radiation source and said detector such that the rays interact with the portion of the pipe assembly and strike said detector, said detector comprising:
        an imaging plate that is activated by illumination with the rays with an exposure between 0.5 Curie-minute and 5 Curie-minutes of radiation, said imaging plate having a thickness between 5 millimeters (mm) and 15 mm; and
        an imaging unit for generating images based on information from said imaging plate, said imaging unit having a pixel pitch that is between 25 microns and 100 microns.

2. The radiography imaging system in accordance with claim 1, further comprising a processor coupled to said detector to facilitate processing the images.

3. The radiography imaging system in accordance with claim 1, wherein said rays have an activity level between 100 kiloelectron-volts (keV) and 500 keV.

4. The radiography imaging system in accordance with claim 3, wherein said imaging unit has a pixel pitch of approximately 50 microns.

5. The radiography imaging system in accordance with claim 4, wherein said imaging unit generates an image having an area of 50.8 mm×101.6 mm (2 inches (in.)×4 in).

6. The radiography imaging system in accordance with claim 4, wherein said radioactive isotope has an activity level of 1 Curie.

7. The radiography imaging system in accordance with claim 6, wherein said radiation source further comprises a close proximity container, said close proximity container comprising a sidewall and a shutter, said sidewall defining an opening therethrough and an interior space, said radioactive isotope positioned in said interior space, said shutter configured to be retractable about the opening between a closed position where rays are inhibited from moving through said opening and an open position where rays are directed through said opening towards said pipe portion and said detector.

8. The radiography imaging system in accordance with claim 7, wherein the radiation source further comprises a guide tube coupled to said close proximity container, said guide tube having a length of 152 mm.

9. The radiography imaging system in accordance with claim 1, wherein said detector further comprises an electronics component and a flex casing, said flex casing comprising a detector enclosure, an electronics enclosure, and a coupling extending between said detector enclosure and said electronics enclosure.

10. A pipe assembly manufacturing facility for assembling a plurality of pipe assemblies, said pipe assembly manufacturing facility comprising:
    at least one assembly area for assembling the plurality of pipe assemblies;
    a radiography imaging system for generating images of the plurality of pipe assemblies, said radiography imaging system comprising:
    a radiation source for emitting rays, said radiation source positioned adjacent at least one pipe assembly of the plurality of pipe assemblies, said radiation source comprising a radioactive isotope having an activity level between 1 Curie and 40 Curies; and;
    a detector positioned opposite said radiation source, a portion of the at least one pipe assembly of the plurality of pipe assemblies positioned between said radiation source and said detector such that the rays interact with the portion of the at least one pipe assembly and strike said detector, said detector comprising:
        an imaging plate that is activated by illumination with the rays with an exposure between 0.5 curie-minute and 5 Curie-minutes of radiation, said imaging plate having a thickness between 5 millimeters (mm) and 15 mm; and
        an imaging unit for generating images based on information from said imaging plate, said imaging unit having a pixel pitch that is between 25 microns and 100 microns; and
    at least one inspection area for inspecting the at least one pipe assembly of the plurality of pipe assemblies using said radiography imaging system, said at least one inspection area contiguous with said at least one assembly area, wherein the at least one pipe assembly remains in said at least one inspection area during operation of said radiography imaging system.

11. The pipe assembly manufacturing facility in accordance with claim 10, further comprising barricades positioned around the at least one inspection area to separate the at least one inspection area from the at least one assembly area and inhibit personnel in the at least one assembly area from entering the at least one inspection area.

12. A method of imaging a pipe assembly using a radiography imaging system, the radiography imaging system including a radiation source and a detector, the radiation source including a radioactive isotope, said method comprising: mounting the radiography imaging system on the pipe assembly such that a portion of the pipe assembly is positioned between the radiation source and the detector; emitting rays from the radiation source such that the rays interact with the pipe assembly and strike the detector, the radioactive isotope having an activity level between 1 Curie and 40 Curies; illuminating the pipe assembly with the rays with an exposure between 0.5 Curie-minute and 5 Curie-minutes of radiation; activating an imaging plate of the detector with the rays; and generating an image of the pipe assembly.

13. The method in accordance with claim 12, wherein emitting rays comprises emitting gamma rays from the radioactive isotope, the gamma rays having an activity level between 100 kiloelectron-volts (keV) and 500 keV.

14. The method in accordance with claim 12, wherein generating an image comprises generating an image having an area of 50.8 mm×101.6 mm (2 inches (in.)×4 in).

15. The method in accordance with claim 14, wherein generating an image of the pipe assembly comprises generating an image of the pipe assembly using an imaging unit having a pixel pitch that is approximately 50 microns.

16. The method in accordance with claim 15, wherein activating the imaging plate comprises activating the imaging plate having a thickness between 5 millimeters (mm) and 15 mm.

17. The method in accordance with claim 12, further comprising inspecting the image to determine characteristics of at least one of a pipe, tubing, and weld on the pipe assembly.

18. The method in accordance with claim 12, further comprising maintaining the activity level of the radiation source at 1 Curie.

19. The method in accordance with claim 18, wherein the radiation source includes a close proximity container including a wall, a pellet, and a shutter, the wall defining an opening therethrough and an interior space, the pellet positioned in the interior space, the shutter configured to be retractable about the opening between a closed position closing the opening and an open position, the method further comprising retracting the shutter to direct rays towards the detector.

20. The method in accordance with claim 19, further comprising directing the pellet through a guide tube and into the interior space of the close proximity container.

* * * * *